United States Patent
Törmälä et al.

(10) Patent No.: US 7,541,049 B1
(45) Date of Patent: Jun. 2, 2009

(54) BIOACTIVE AND BIODEGRADABLE COMPOSITES OF POLYMERS AND CERAMICS OR GLASSES AND METHOD TO MANUFACTURE SUCH COMPOSITES

(75) Inventors: Pertti Törmälä, Tampere (FI); Minna Kellomäki, Tampere (FI); William Bonfield, Welwyn (GB); Kathleen Elizabeth Tanner, London (GB)

(73) Assignee: Linvatec Biomaterials Oy, Tampere (FR)

( * ) Notice: Subject to any disclaimer, the term of this patent is extended or adjusted under 35 U.S.C. 154(b) by 646 days.

(21) Appl. No.: 08/921,533

(22) Filed: Sep. 2, 1997

(51) Int. Cl.
*A61F 2/00* (2006.01)
*A61F 13/00* (2006.01)
*A61B 2/02* (2006.01)

(52) U.S. Cl. .................. 424/426; 424/422; 623/23.75; 623/11.11

(58) Field of Classification Search .............. 424/424, 424/426, 422; 606/77, 13, 16
See application file for complete search history.

(56) References Cited

U.S. PATENT DOCUMENTS

| | | | | |
|---|---|---|---|---|
| 4,239,113 A | * | 12/1980 | Gross et al. | 206/580 |
| 4,400,833 A | | 8/1983 | Kurland | |
| 4,612,923 A | * | 9/1986 | Kronenthal | 606/77 |
| 4,743,257 A | * | 5/1988 | Tormala et al. | 623/23.58 |
| 4,778,471 A | * | 10/1988 | Bajpai | 424/423 |
| 4,898,186 A | | 2/1990 | Ikada et al. | 606/62 |
| 4,968,317 A | * | 11/1990 | Tormala et al. | 606/77 |
| 5,084,051 A | * | 1/1992 | Tormala et al. | 606/77 |
| 6,406,498 B1 | * | 6/2002 | Tormala et al. | 623/23.75 |

FOREIGN PATENT DOCUMENTS

| | | |
|---|---|---|
| EP | 0274898 | 7/1988 |
| GB | 2085461 | 4/1982 |
| WO | WO 90/04982 | 5/1990 |
| WO | WO 90/12605 | 11/1990 |
| WO | WO94/15588 | 7/1994 |
| WO | WO 96/00592 | 1/1996 |
| WO | WO96/41596 | 12/1996 |
| WO | WO98/14134 | 4/1998 |
| WO | WO 98/30252 | 7/1998 |

OTHER PUBLICATIONS

Bonfield et al. In vivo evaluation of hydroxyapatite reinforced polyethylene composites. Biological and Biomechanical Performance of Biomaterials. Ed. P. Christel et al. Elsevier Science Publishers B.V., Amsterdam. pp. 153-158, 1986.*

(Continued)

*Primary Examiner*—Lakshmi S Channavajjala
(74) *Attorney, Agent, or Firm*—Kenyon & Kenyon LLP

(57) ABSTRACT

Surgical osteosynthesis composite material which has three components: biodegradable polymer reinforcement, bioceramic or bioglass filler reinforcement and biodegradable polymer matrix. This invention relates to biodegradable materials used for bone fracture fixation devices and methods of their manufacture. Unlike other known materials used prior to this application, the composites of this invention have two different reinforcing phases and one matrix phase. One reinforcing element is referred as the polymeric reinforcing element and the other as the ceramic reinforcing element.

16 Claims, 2 Drawing Sheets

○ Fibrillated polymer reinforcement

▦ Mixture of matrix polymer and bioceramic or glass

OTHER PUBLICATIONS

R.M. Pilliar, Powder Metal-Made Orthopedic Implants with Porous Surface for Fixation by Tissue Ingrowth, Clinical Orthopaedics and Related Research, vol. I 176, 1983, pp. 42-51.

S. Vainiopaa, et al, Surgical Applications of Biodegradable Polymers in Human Tissues, Progress in Polymer Science, vol. 14, 1989, pp. 679-716.

J. Eitenmüller, et al., An In Vivo Evaluation of a New High Molecular Wt. Polylactide Osteosynthesis Device, European Congress on Biomaterials, Bologna Italy, Sep. 14-17, 1986, p. 94.

Törmälä, Biodegradable Self-Reinforced Composite Materials; Manufacturing Structure & Mechanical Properties, Clinical Materials, vol. 10, 1992, pp. 29-34.

O.H. Andersson, et al., Bioactive Glass, Biomaterials Today and Tommorrow, Proceedings of the Finnish Dental Society Days of Research, Tampere, Finland, Nov. 10-11, 1995, pp. 15-16.

J.C. Behiri, et al., Advanced Bone Cement For Long Term Orthopaedic Applications, Bioceramics, vol. 4 Edited by W. Bonfield, et al., Proceedings of the 4th International Symposium on Ceramics in Medicine, London, UK, Sep. 1991, Butterworth—Heinemann Ltd., Oxford, 1991, pp. 301-307.

W. Bonfield, et al., In Vivo Evaluation of Hydroxyapatite Reinforced Polyethylene Composites, Biological & Biomechanical Performance of Biomaterials, Edited by P. Christel, et al., Elsevier Science Publishers, 1986, pp. 153-158.

C. Doyle, et al., In Vitro & In Vivo Evaluation of Polyhydroxybutyrate and of Polyhydroxybutyrate Reinforced with Hydroxyapatite, Biomaterials, vol. 12, 1991, pp. 841-847.

International Search Report for PCT/EP98/05440.

Chase S. W., Herndon C.H., "The fate of autogenous and homogenous bone grafts: A historical review," *Journal of Bone Joint Surgery* 37 A, 1955, pp. 809-841.

Prolo D.J., "Cranial defects and cranioplasty, in Wilkins RH, Rengachary SS (eds): Neurosurgery," New York, McGraw-Hill, 1984, pp. 1647-1656.

Grant F.C., Norcross N.C., "Repair of Cranial Defects By Cranioplasty," *Annual Surgery* vol. 110, 1939, pp. 488-512.

Reeves D.L., "Cranioplasty," Springfield, IL, Charles C. Thomas, 1950, pp. 3-119.

Woolf J.I., Walker A.E., "Cranioplaty, Collective review," *International Abstracts Surgery* 81, 1945, pp. 1-23.

Habal M.B., Leake D.L., Maniscako J.E., "A new method for reconstruction of major defects in the cranial vault," *Surgery Neurology* 6, 1976, pp. 137-138.

Karvounis P.C., Chiu J., Sabin H., "The use of prefabricated polyethylene plate for cranioplasty," *Journal of Trauma* 10, 1970, pp. 249-254.

Black S.P.W., "Reconstruction of the supraorbital ridge using aluminum," *Surgery Neurology* 9, 1978, pp. 121-128.

Heller J., Poloy(ortho esters), Advances in Polymer Science 107: 41-92, 1993.

Peter D. Costantino, et al. "Synthetic biomaterials in Facial Plastic and reconstructive Surgery." *Facial Plastic Surgery* vol. 9, No. 1. Jan. 1993, pp. 1-15.

P. Törmälä et al., "Bioabsorbable polymers: materials technology and surgical applications," Proc. Instn. Mech. Engers., vol. 212, Part H., pp. 101-111.

S. Paasimaa et al., Development of a Bioabsorbable Finger Joint Prosthesis: Material Selection, 13$^{th}$ European Conf. On Biomaterials, Sep. 4-7, 1977, pp. 146.

Rogers et al., "Absorbable Mesh Splenorrhaphy for Server Splenic Injuries: Functional Studies in an Animal Model and an Additional Patient Series," The Journal of Trauma, vol. 31, No. 2, 1991, pp. 200-204.

Nagy et al., "Experience with Three Prosthetic Materials in Temporary Abdominal Wall Closure," The American Surgeon, vol. 2, May, 1996, pp. 331-335.

Rahman, et al., "Silicone Granulomatous Reactions After First Metatarsophalangeal Hemiarthroplasty," British Editorial Society of Bone and Joint Surgery, Vo. 75-B, No. 4, Jul. 1993, pp. 637-639.

Kossovsky et al., "An Unusual Case of Biomaterials Pathology Discovered at Autopsy Using X-Ray Energy Spectroscopic Techniques," Biomaterials Bioreactivity Characterization Laboratory and Division of Anatomic Pathology, Apr. 7, 1989, pp. 148-152.

Ashammakhi et al., "Strength retention of self-reinforced polyglycolide membrane: an experimental study," Biomaterials 1995, vol. 16, No. 2, pp. 135-138.

Pizzoferrato et al, "Biomaterials and Clinical Applications," Proceedings of the Sixth European Conference on Biomaterials, Bologna, Italy, Sep. 14-17, 1986; 759-764.

McDowell et al., "The McDowell Series of Plastic Surgical Indexes," vol. 1, The Zeis Index and History of Plastic Surgery 900 B.C.-1863 A.D., pp. 51-52.

\* cited by examiner

○ Fibrillated polymer reinforcement

▨ Mixture of matrix polymer and bioceramic or glass

BIOACTIVE AND BIODEGRADABLE COMPOSITES OF POLYMERS AND CERAMICS OR GLASSES AND METHOD TO MANUFACTURE SUCH COMPOSITES

FIELD OF THE INVENTION

The present invention relates to a surgical osteosynthesis composite material, which is biodegradable and bioactive, and methods of manufacturing the composite material.

BACKGROUND OF THE INVENTION

In surgery, either biostable or biodegradable devices are used for the fixation of bone fractures to immobilize the bone fragments and accelerate patient mobilization.

Most biostable devices are typically made of metallic alloys. See R. M. Pilliar, Powder Metal-Made Orthopaedic Implants With Porous Surface For Fixation By Tissue Ingrowth, Clinical Orthopaedics and Related Research, Vol. 176, 1983, pp. 42-51. Nevertheless, there are several disadvantages in the use of metallic implants. One such disadvantage is bone resorption caused by bone plates and screws, which carry most of the external loads, leading to stress protection produced by the modulus mismatch between metals and bone. Another disadvantage is the carcinogenic potential and the possibility of corrosion. Therefore, surgeons are recommended to remove metallic bone plates and screws in a second operation once the fracture has healed.

Bioresorbable polymeric fracture fixation devices have been studied as replacements for metallic implants. See S. Vainiopää, P. Rokkanen, P. Törmälä, Surgical Applications Of Biodegradable Polymers In Human Tissue, Progress in Polymer Science, Vol. 14, 1989, pp. 679-716. The advantages of these devices are that materials resorb in the body and degradation products disappear via metabolic routes. Hence, a second operation is not required. Additionally, the strength and the stiffness of the bioresorbable polymeric devices decreases when the device degrades and hence the bone is progressively loaded (which promotes bone regeneration). One disadvantage is the relatively low strength of existing polymeric devices. In the case of cortical, bone fracture, for example, unreinforced poly lactic acid (PLLA) plate and screws are too weak initially to permit patient mobilization. See J. Eitenmüller, K. L. Geriach, T. Scmickal, H. Krause, An In Vivo Evaluation Of A New High Molecular Weight Polylactide Osteosynthesis Device, European Congress on Biomaterials, Bologna Italy, Sep. 14-17, 1986, p. 94. In addition, the relatively low values of Young's modulus compared to metallic plates mean that thicker sections are required to ensure adequate stability.

Törmälä et al. have developed self-reinforced bioresorbable polymeric composites to improve the strength of bioresorbable polymer devices. These show good mechanical properties: e.g. bending strengths of 360±70 MPa and bending moduli of 12±2 GPa, respectively, have been reported. See P. Törmälä, Biodegradable Self-Reinforced Composite Materials; Manufacturing, Structure and Mechanical Properties, Clinical Materials, Vol. 10, 1992, pp. 29-34.

A common property of most polymeric implants is the lack of bony ongrowth to the material. In contrast, such bone apposition is produced by bioactive ceramics and glasses. See O. H. Andersson, K. H. Karlsson, Bioactive Glass, Biomaterials Today And Tomorrow, Proceedings of the Finnish Dental Society Days of Research, Tampere, Finland, 10-11 Nov. 1995, Gillot Oy, Turku, 1996, pp. 15-16. By adding bioactive ceramics or glasses to polymers to produce a composite, the bioactivity of the material can be improved. This effect has been demonstrated in dental composites and bone cement. See J. C. Behiri, M. Braden, S. N. Khorashani, D. Wiwattanadate, W. Bonfield, Advanced Bone Cement For Long Term Orthopaedic Applications, Bioceramics, Vol. 4, ed. W. Bonfield, G. W. Hastings and K. E. Tanner, Butterworth-Heinemann ltd, Oxford, 1991, pp. 301-307.

Bonfield et al have developed a biostable composite consisting of a polyethylene matrix and a particulate hydroxyapatite reinforcement (HAPEX™). See W. Bonfield, J. A. Bowman, M. D. Grynpas, UK Patent GB2085461, 1984. HAPEX™ composites show bioactivity above 0.20 volume fraction hydroxyapatite. See W. Bonfield, C. Doyle, K. E. Tanner, In Vivo Evaluation Of Hydroxyapatite Reinforced Polyethylene Composites, Biological and Biomechanical Performance of Biomaterials, ed., P. Christel, A. Meunier, A. J. C. Lee, Elsevier Science Publisher, 1986, pp. 153-158. Additionally, degradable composites of hydroxyapatite and copolymers of polyhydroxybutyrate and polyhydroxyvalerate have been described. See C. Doyle, K. E. Tanner, W. Bonfield, In Vitro And In Vivo Evaluation Of Polyhydroxybutyrate And Polyhydroxybutyrate Reinforced With Hydroxyapatite, Biomaterials, Vol. 12, 1991, pp. 841-847. The main limitation of these biostable and biodegradable composites is their inadequate mechanical strength for large bone fracture fixation. Also, use of hydroxyapatite and poly lactic acid composites has been reported. See Y. Ikada, H. H. Suong, Y. Shimizu, S. Watanabe, T. Nakamura, M. Suzuki, A. T. Shimamoto, Osteosynthetic Pin, U.S. Pat. No. 4,898,186, 1990. Using existing elements the composite still has quite moderate mechanical strength. Also in all these cases mentioned above the method of producing the composite differs from the method of the present invention.

SUMMARY OF THE INVENTION

In this invention, we have established that the problems of inadequate strength and the brittleness of the bioactive bone fixation devices and the lack of bioactivity of absorbable polymeric devices are resolved by constructing a composite material comprising at least one resorbable polymeric matrix, at least one bioactive ceramic reinforcing element and at least one resorbable polymeric reinforcing component. The composite material described in more detail herein consists of two reinforcing components in a matrix material. One reinforcing element, the polymeric reinforcing element, is comprised of biodegradable polymer fiber and the other, called the ceramic reinforcing element, is comprised of bioceramic or bioglass. Reinforced composite devices described in this invention have improved mechanical properties compared to non-reinforced devices, because reinforcement changes the behavior of material from brittle to ductile and thus makes device more reliable under load. Due to controlled manufacturing stages, mixing of matrix and ceramic reinforcing element as well as combining the polymeric reinforcing element, the amount of both reinforcing element types is easily controlled. This is an important advantage, because the ratio of elements affects the mechanical properties of the device. Also, the amount of the ceramic reinforcing element affects the bioactivity of the device.

DESCRIPTION OF THE PREFERRED EMBODIMENTS

Figure 1:
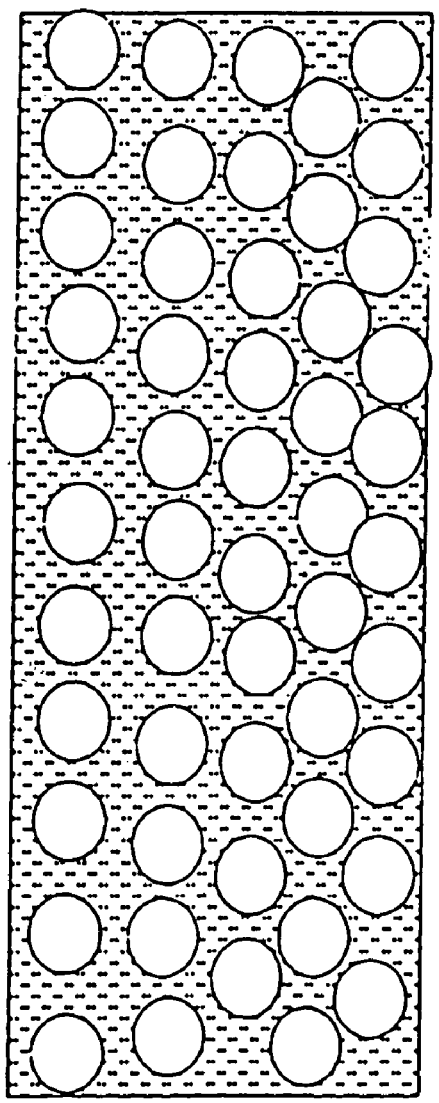
FIG. 1 Shows a schematic picture of the cross-section of a composite plate of the invention.

This invention relates to biodegradable materials used for bone fracture fixation devices and methods of their manufacture. Unlike other known materials used prior to this application, the composites of this invention have two different reinforcing phases and one matrix phase. One reinforcing element is referred as the polymeric reinforcing element and the other as the ceramic reinforcing element. The matrix component can be any biodegradable or bioerodible polymer. Typical examples of these polymers are listed in Table 1 herein.

One reinforcing phase is a totally or at least partially oriented and/or fibrillated biodegradable or bioerodible polymer. This phase is called the polymeric reinforcing element, which is still recognizable and distinguishable from the final product as a whole. The diameter of the reinforcing fibers can vary between 4 µm and 800 µm, preferably between 20 µm and 500 µm. Useful polymers for the polymeric reinforcing element include those listed in Table 1.

The ceramic reinforcing element can be comprised of a stable or a degradable bioceramic or bioglass, or a mixture of these. Typical examples are listed in Table 2. They can be used in a powder, flake, spherical, fiber or any other form. Particle size can vary between 2 µm and 100 µm, preferably between 60 µm and 150 µm. In the case of fibers, the fibers are in all cases smaller than the polymeric reinforcing elements. The ceramic reinforcing element also acts as a bioactive, bony ongrowth agent and provides a reservoir of calcium and phosphate ions, thus accelerating the healing time for bone fractures. While the matrix polymer degrades, bone can attach to the residual ceramic or glass particles. The amount of ceramic reinforcing element is 0.15 to 0.9 volume fraction, preferably between 0.2 and 0.6 volume fraction.

The defined particle size of the ceramic element in the composite described in this invention is relatively big compared to conventionally used particle sizes for fillers or granules. In this invention, it was found unexpectedly that composites having bigger particle size ceramic elements are more biocompatible and cause less irritation to tissue than composites utilizing a ceramic element having small particle size. Biocompatibility is easily seen in histological studies. In tissue near and inside the degrading composite implants having small ceramic particles there exists more giant cells than around and inside the degrading composite implants containing big (coarser) ceramic particles.

The invention may contain various additives and modifiers which improve the processability of the composite. Such additives include surface modifiers to improve the attachment between the polymeric and ceramic components. The devices can also contain pharmaceutically active agent or agents, such as antibiotics, chemotherapeutic agents, wound-healing agents, growth hormones and anticoagulants (such as heparin). These agents are used to enhance the bioactive feature of the composite and thus improve the healing process of the tissue.

Manufacture of the composite can be performed by any suitable plastics technology processing method. The matrix polymer and the ceramic reinforcing element(s) (bioceramic or bioglass) can be mixed together by powder mixing, melt mixing or solvent mixing. The polymeric reinforcing element (polymer fiber) can be used as plain fiber or in modified form: for example, as braided or woven two or three dimensional structures. The mixture of matrix and the ceramic reinforcing element can be combined with the polymeric reinforcing element by melt mixing, by coating or by using solvent as an intermediate to preform the material (prepreg). The material can be produced in its final form by various techniques, including compression molding, filament winding, mechanical machining or injection molding to any desired shape.

Due to controlled manufacturing stages, mixing of matrix and ceramic reinforcing element as well as combining the polymeric reinforcing element, the amount of both reinforcing element types is easily controlled. This is an important advantage, because the ratio of elements affects the mechanical properties of the device. Also, the amount of the ceramic reinforcing element affects the bioactivity of the device. There should be sufficient bioceramic or bioglass to yield bony ongrowth.

Reinforced composite devices described in this invention have improved mechanical properties compared to non-reinforced devices, because reinforcement changes the behavior of the material from brittle to ductile and thus makes the reinforced device more reliable under load. This feature is very important for load bearing applications, such as bone fracture fixation devices. For example, non-reinforced poly lactic acid devices typically have three-point bending strengths of 35-40 MPa and moduli of 3.5-4.0 GPa, and particulate reinforced (hydroxyapatite) poly lactic acid devices have values of 25-30 MPa and 5.0 GPa, respectively. Using polymer fiber reinforcement under the present invention, mechanical properties of two to five times higher are achieved.

EXAMPLES

The present invention is described in more detail by means of the following, non-limiting examples.

Example 1

Plates sized approximately 50×10×2 mm were manufactured by compression molding from a powder mixture of poly (L,D-lactide) (95/5 L/D ratio) and hydroxyapatite with particle size of 60 µm, reinforced unidirectionally with poly (L-lactide) fibers (53/35/12 weight percent of matrix polymer-hydroxyapatite-polymer fiber, respectively). Three-point bending strength (yield) and modulus were 69.8 MPa and 5.8 GPa, respectively, and no sample fracture was detected (ductile behavior). These results were compared to the results of similarly sized samples without fiber reinforcement, compression molded from (1) plain PLDLA 95/5 and from (2) powder mixture of PLDLA 95/5 and hydroxyapatite (60/40 w/w %). These samples showed three-point bending strengths (maximum) and moduli of (1): 38.0 MPa and 3.9 GPa and (2): 26.8 MPa and 5.0 GPa, respectively. These samples broke in bending without yielding, thus showing brittle fracture behavior.

Example 2

Plates sized as in example 1 were manufactured by compression molding from a mixture of poly (L,D-lactide) (85/15 L/D ratio) and hydroxyapatite with particle size of 60 µm reinforced unidirectionally with poly (L-lactide) fibers. Poly (L,D-lactide) and hydroxyapatite were previously melt mixed to a film form. The composition had 48/21/31 weight percent of matrix polymerhydroxyapatite-polymer fibers, respectively. Three-point bending strength (yield) and modulus were 116.6 MPa and 6.1 GPa, respectively, and no sample fracture was detected.

Example 3

Plates sized approximately 50×10×1 mm were manufactured by compression molding from the unidirectional prepreg material of poly (L,D lactide) (85/15 L/D ratio), hydroxyapatite and poly (L-lactide) fibers. The proportions of components varied from 3-16 wt-%, 15-50 wt-% and 48-85 wt-%, respectively. Three-point bending strength (yield) and modulus depended on the concentrations of the composite. Typical mechanical properties are listed in Table 3. No sample fracture was detected and the behavior was ductile.

TABLE 3

| PLDLA (85/15) matrix (wt-%) | PLLA fibers (wt-%) | Hydroxy apatite (wt-%) | Three-point bending strength (MPa) | Three-point bending modulus (GPa) |
| --- | --- | --- | --- | --- |
| 3 | 82 | 15 | 136 | 9.5 |
| 4 | 71 | 25 | 143 | 9.1 |
| 5 | 47 | 48 | 141 | 12.2 |
| 8 | 61 | 31 | 139 | 10.5 |
| 9 | 54 | 37 | 118 | 8.3 |
| 16 | 48 | 36 | 166 | 9.6 |

Example 4

Plates sized as in example 3 were manufactured by compression molding from a prepreg material of poly (L,D-lactide) (85/15 L/D ratio), hydroxyapatite and poly (L-lactide) fibers. The proportions of components were 4 wt-%, 15 wt-% and 81 wt-%, respectively. Three sample types were manufactured having different prepreg lay-ups of 0°/0°/0°/0°/0°, 0°/45°/0°/−45°/0° and 0°/0°/90°/0°/0°. Three-point bending strengths (yield) and moduli were 135.9 MPa and 9.5 GPa, 140.1 MPa and 10.1 GPa, and 131.0 MPa and 9.3 GPa, respectively, and no sample fracture was detected.

Example 5

The surfaces of three different samples were studied by Fourier Transform Infrared Spectroscopy. Samples were:
a) hydroxyapatite
b) hydroxyapatite-poly (D,L-lactide)-poly (L-lactide) composite
c) poly (D,L-lactide)-poly (L-lactide) composite.

Figure 2:
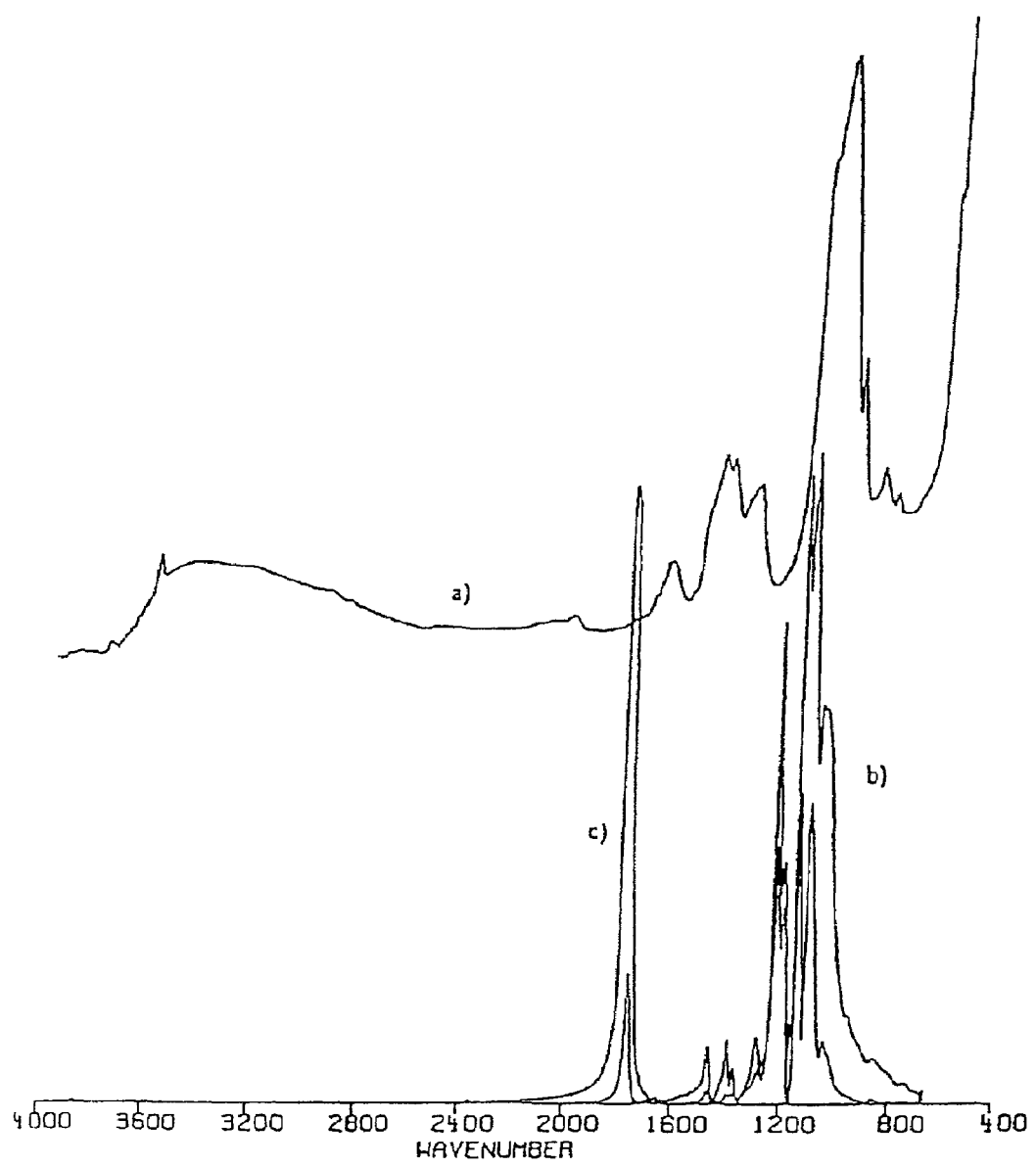
FIG. 2a Shows a FTIR spectrum of hydroxyapatite.
FIG. 2b Shows a FTIR spectrum of hydroxyapatite-poly lactic acid composite.
FIG. 2c Shows a FTIR spectrum of poly lactic acid composite.

The spectras from these samples are shown in FIG. 2. Matching peaks are detectable with samples b and c, which are poly lactide peaks. There also occur matching peaks from samples a and b which are characteristic of calcium phosphate compounds. The bioactivity of the composites claimed in this invention is the result of hydroxyapatite on the surface.

Example 6

Plates sized as in example 3 were manufactured by compression molding from the unidirectional prepreg material of racemic poly (D,L-lactide), tricalcium phosphate with mean particle size of 70 μm and poly glycolide fibers. The proportions of components varied from 5 wt-%, 20 wt-% and 75 wt-%, respectively. Three-point bending strength (yield) and modulus were 195 MPa and 14.2 GPa, and no sample fracture was detected.

Example 7

Plates sized as in example 3 were manufactured by compression molding from the prepreg material made of racemic poly (D,L-lactide), hydroxyapatite powder with mean particle size of 100 μm and the fabric made of poly (L-lactide) and poly (L,D lactide) (96/4) fibers. The proportions of components varied from 5 wt-%, 20 wt-% and 75 wt-%, respectively. Three-point bending strength (yield) and modulus were 150 MPa and 11.8 GPa, and no sample fracture was detected. Specimens showed, similar mechanical properties in both the warp and the weft directions of the fabric.

Example 8

Plates sized as in example 1 were manufactured by compression molding from a mixture of poly (ortho ester) and hydroxyapatite with mean particle size of 80 μm reinforced unidirectionally with poly (ortho ester) fibers. Poly (ortho ester) matrix and hydroxyapatite were previously melt mixed to a film form. The composition had 50/20/30 weight percent of matrix polymerhydroxyapatite-polymer fibers, respectively. Three-point bending strength (yield) and modulus were 105 MPa and 9.7 GPa, respectively, and no sample fracture was detected.

Example 9

Plates sized as in example 3 were manufactured by compression molding from the unidirectional prepreg material of copolymer of poly (D,L lactide) and poly-e-caprolactone, tricalcium phosphate with mean particle size of 80 μm and poly-e-caprolactone fibers. The proportions of components varied from 16 wt-%, 30 wt-% and 54 wt-%, respectively. Three-point bending strength (yield) and modulus were 86 MPa and 3.4 GPa, and no sample fracture was detected. The strength and modulus values were lower than those for lactide based composites, but the extension to yield was much higher.

Example 10

Plates sized as in example 1 were manufactured by compression molding from a mixture of a copolymer of poly (hydroxybutyrate)-poly (hydroxyvalerate) and a mixture of hydroxyapatite and tricalcium phosphate (50/50) with mean particle size of 120 μm, reinforced unidirectionally with poly (hydroxybutyrate) fibers. The polymer matrix and ceramic mixture were previously melt mixed to a film form. The composition had 30/30/40 weight percent of matrix copolymer-ceramic mixture-polymer fibers, respectively. Three-point bending strength (yield) and modulus were 122 MPa and 6.2 GPa, respectively, and no sample fracture was detected.

Example 11

Two set of samples (plates with 5 mm width, 20 mm length and 0.9 mm thickness) were implanted to the back of rats (subcurris). Specimens were made of poly-L lactic acid fibers, poly-D,L-lactic acid matrix (with L/D ratio 85/15) and hydroxyapatite powder using prepreg manufacturing method. The quantities of the components were 80 wt-%, 5 wt-% and 15 wt-%, respectively. The plates had five prepreg layers, with layer alignments of 0°/0°/0°/0°/0°. The mean particle diameter of hydroxyapatite powder in the first set of plates was 7.43 micrometers and in the second set of plates was 80±20 micrometers. The plates were gamma sterilized with a dose of 2.5 MRads.

Five animals from both sets were sacrificed after one year of implantation. In histological studies it was clearly seen, that in and around the composite plates with finer hydroxyapatite powder there existed significantly more giant cells than in the tissue of reference animals containing composite plates with coarser hydroxyapatite particles. Thus, coarser hydroxyapatite particles were shown to be more biocompatible.

TABLE 1

Resorbable polymers suitable for biocomposites.

Polymer
Polyglycolide (PGA)
Copolymers of glycolide:

Glycolide/L-lactide copolymers (PGA/PLLA)
Glycolide/trimethylene carbonate copolymers (PGA/TMC)
Polylactides (PLA)
Stereocopolymers of PLA:

Poly-L-lactide (PLLA)
Poly-DL-lactide (PDLLA)
L-lactide/DL-lactide copolymers
Copolymers of PLA:
Lactide/tetramethylglycolide copolymers
Lactide/trimethylene carbonate copolymers
Lactide/d-valerolactone copolymers
Lactide/e-caprolactone copolymers
PLA/polyethylene oxide copolymers
Polydepsipeptides
Unsymmetrically 3,6-substituted poly-1,4-dioxane-2,5-diones
Poly-b-hydroxybutyrate (PHB)
PHB/b-hydroxyvalerate copolymers (PHB/PHV)
Poly-b-hydroxypropionate (PHPA)
Poly-p-dioxanone (PDS)
Poly-d-valerolactone
Poly-e-caprolactone
Methylmethacrylate-N-vinyl pyrrolidone copolymers
Polyesteramides
Polyesters of oxalic acid
Polydihydropyrans
Polyalkyl-2-cyanocrylates
Polyurethanes (PU)
Polyvinylalcohol (PVA)
Polypeptides
Poly-b-malic acid (PM LA)
Poly-b-alkanoic acids
Polycarbonates
Polyorthoesters
Polyphosphates

TABLE 2

Bioceramics and glasses suitable for biocomposites.

Hydroxyapatite
Tricalcium phosphate
Other calcium phosphates
Bioglass ®
Ceravital ®
Alumina
Zirconia
Bioactive gel-glass
Bioactive glasses
Alpha wollastonite glass ceramic

What is claimed is:

1. A biodegradable and bioactive composite material for surgical osteosynthesis applications comprising: i) at least one resorbable polymeric matrix component, ii) at least one resorbable polymeric reinforcing component in fiber form, and iii) at least one bioceramic or bioglass reinforcing component mixed with said matrix component, the diameter of the resorbable polymeric reinforcing component being greater than the diameter or particle size of the bioceramic or bioglass reinforcing component, wherein the bioceramic or bioglass reinforcing component has a particle size between 60 μm and 150 μm.

2. A method of manufacturing a biodegradable composite according to claim 1, comprising the steps of:
a) selecting at least one first polymer for the matrix;
b) selecting at least one bioceramic material, bioglass material or mixture thereof for use as the bioceramic or bioglass reinforcing component;
c) mixing said first polymer and said bioceramic or bioglass reinforcing component together to form a mixture;
d) selecting at least one second polymer in a fiber form for the resorbable polymeric reinforcing component;
e) placing said second polymer into a desired formation;
f) combining said mixture of step (c) and said formation of step (e) to yield a second mixture; and
g) subjecting the second mixture of step (f) to heat or pressure.

3. The composite material according to claim 1 wherein the at least one resorbable polymeric reinforcing component comprises at least one fiber having a variable thickness.

4. The composite material according to claim 1 wherein the at least one resorbable polymeric reinforcing component is selected from the group consisting of a fabric, a plain polymeric fiber structure, a woven structure and a braided structure.

5. The composite material according to claim 1 wherein the form of the bioceramic or bioglass reinforcing component is selected from the group consisting of powder, flakes, spheres and fibers.

6. The composite material according to claim 1 wherein the amount of bioceramic or bioglass reinforcing component is 0.15 to 0.9 volume fraction.

7. The composite material according to claim 6 wherein the amount of bioceramic or bioglass reinforcing component is 0.2 to 0.6 volume fraction.

8. The composite material according to claim 1 further comprising additives selected from the group consisting of surface modifiers to improve attachment between the resorbable polymeric reinforcing component and the bioceramic or bioglass reinforcing component, a pharmaceutically active agent, and combinations thereof.

9. The composite material according to claim 8 wherein the pharmaceutically active agent is selected from the group consisting of antibiotics, wound-healing agents, chemotherapeutic agents, growth hormones, anticoagulants, and combinations thereof.

10. The composite material according to claim 1 wherein the resorbable polymeric matrix component is selected from the group consisting of polyglycolide, copolymers of glycolide, glycolide/L-lactide copolymers, glycolide/trimethylene carbonate copolymers, polylactides, stereocopolymers of polylactides, poly-L-lactide, poly-DL-lactide, L-lactide/DL-lactide copolymers, copolymers of polylactides, lactide/tetramethylglycolide copolymers, lactide/trimethylene carbonate copolymers, lactide/d-valerolactone copolymers, lactide/e-caprolactone copolymers, polylactide/polyethylene oxide copolymers, polydepsipeptides, unsymmetrically 3,6-substituted poly-1,4-dioxane-2,5-diones, poly-b-hydroxybutyrate, poly-b-hydroxybutyrate/b-hydroxyvalerate copolymers, poly-b-hydroxypropionate, poly-p-dioxanone, poly-d-valerolactone, poly-e-caprolactone, methylmethacrylate-N-vinyl pyrrolidone copolymers, polyesteramides, polyesters of oxalic acid, polydihydropyrans, polyalkyl-2-cyanocrylates, polyurethanes, polyvinylalcohol, polypeptides, poly-b-malic acid, poly-b-alkanoic acids, polycarbonates, polyorthoesters and polyphosphates.

11. The composite material according to claim 1 wherein the bioceramic or bioglass reinforcing component is selected from the group consisting of hydroxyapatite, calcium phosphates, alumina, zirconia, bioactive gel-glass, alpha wollastonite glass ceramic, and mixtures of bioglass and bioceramic materials.

12. The composite material according to claim 1 wherein the composite material exhibits ductile behavior under load.

13. The method according to claim 2 wherein the mixing of step c) is accomplished by melt mixing.

14. The method according to claim 2 wherein the mixing of step c) is accomplished by solvent mixing.

15. The method according to claim 2 wherein step e) is accomplished manually.

16. The method according to claim 2 wherein step e) is accomplished with use of a machine.

* * * * *